(12) United States Patent
Poon et al.

(10) Patent No.: US 9,539,525 B2
(45) Date of Patent: Jan. 10, 2017

(54) CENTRIFUGATION DEVICE AND METHODS FOR ISOLATION OF BIOMASS FROM ALGAE MIXTURE AND EXTRACTION OF OIL FROM KITCHEN RESIDUE

(71) Applicant: PETROLEUM 2.0 LIMITED, Hong Kong (HK)

(72) Inventors: Wing Hei Dennis Poon, Hong Kong (HK); Gang Luo, Hong Kong (HK); Cheung Tung Chung, Hong Kong (HK); Tung Ning Tony Tse, Hong Kong (HK)

(73) Assignee: PETROLEUM 2.0 LIMITED, Hong Kong (HK)

(*) Notice: Subject to any disclaimer, the term of this patent is extended or adjusted under 35 U.S.C. 154(b) by 20 days.

(21) Appl. No.: 14/730,267

(22) Filed: Jun. 4, 2015

(65) Prior Publication Data
US 2015/0353865 A1 Dec. 10, 2015

Related U.S. Application Data

(60) Provisional application No. 62/008,500, filed on Jun. 5, 2014.

(51) Int. Cl.
| | |
|---|---|
| *B01D 21/26* | (2006.01) |
| *B01D 21/00* | (2006.01) |
| *C11B 3/00* | (2006.01) |
| *C12N 1/02* | (2006.01) |
| *C11B 1/02* | (2006.01) |
| *C12N 1/12* | (2006.01) |

(Continued)

(52) U.S. Cl.
CPC ......... *B01D 21/262* (2013.01); *B01D 21/0012* (2013.01); *B01D 21/0042* (2013.01); *B01D 21/2483* (2013.01); *B04B 3/00* (2013.01); *C11B 1/025* (2013.01); *C11B 3/00* (2013.01); *C11B 3/008* (2013.01); *C11B 3/16* (2013.01); *C11B 13/00* (2013.01); *C12N 1/02* (2013.01); *C12N 1/12* (2013.01); *Y02W 30/74* (2015.05)

(58) Field of Classification Search
CPC ............. B01D 21/0042; B01D 21/262; B01D 21/2483; B01D 21/0012; C11B 13/00; C11B 1/025; C11B 3/00; C11B 3/008; C11B 3/16; C12N 1/02; C12N 1/12; B04B 3/00; Y02W 30/74
See application file for complete search history.

(56) References Cited

U.S. PATENT DOCUMENTS 3,069,226 A * 12/1962 Boucher ................ B01D 35/00
210/748.11
3,269,420 A * 8/1966 Woodling ............... F15D 1/065
138/38

(Continued)

*Primary Examiner* — John Kim

(57) ABSTRACT

A centrifugation device includes a feeding tube defining a longitudinal axis, and a plurality of centrifugal plates extending longitudinally and radially around the feeding tube and rotatable about the longitudinal axis. The centrifugal plates have coarse surfaces coated with one or more layers of polymer material. A centrifugation tank is disposed coaxially with the feeding tube and around the centrifugal plates. A sidewall of the tank is provided with micro/nano filters. Methods for isolation of algal biomass from an algae and aqueous mixture, and extraction of oil from kitchen residue and/or microalgae are also disclosed.

13 Claims, 23 Drawing Sheets

(51) Int. Cl.
*C11B 3/16* (2006.01)
*C11B 13/00* (2006.01)
*B01D 21/24* (2006.01)
*B04B 3/00* (2006.01)

(56) References Cited

U.S. PATENT DOCUMENTS

| | | | |
|---|---|---|---|
| 2006/0003053 A1* | 1/2006 | Ekanayake | A21D 2/36 426/51 |
| 2012/0048805 A1* | 3/2012 | McCutcheon | B01D 67/0088 210/654 |
| 2012/0064213 A1* | 3/2012 | Lee | B04B 3/04 426/472 |
| 2014/0174468 A1* | 6/2014 | Park | B08B 7/04 134/6 |

* cited by examiner

* Polyvinyl chloride (PVC) acts as primer on the surface of stainless steel

CENTRIFUGATION DEVICE AND METHODS FOR ISOLATION OF BIOMASS FROM ALGAE MIXTURE AND EXTRACTION OF OIL FROM KITCHEN RESIDUE

CROSS-REFERENCE TO RELATED APPLICATIONS

This application claims the benefit of U.S. Provisional Patent Application No. 62/008,500 filed Jun. 5, 2014, the entire content of which is hereby incorporated by reference.

FIELD OF THE TECHNOLOGY

The present application relates to a centrifugation device. In particular, it relates to a centrifugation device and methods for isolation of algal biomass from an algae and aqueous mixture, and extraction of oil from kitchen residue and/or microalgae.

BACKGROUND

Depletion of fossil fuel and greenhouse effect disturb the human race for the past few decades. Scientists keep seeking environmental-friendly regenerative fuels and new sources of energy to resolve this urgent matter. Algal based fuel is classified as third to fourth class regenerative fuel due to high cost and energy ineffectiveness. In fact, the reason behind this is that high energy is required in separating aqueous medium and algal biomass, generally of about 25 MJ/kg. Therefore, a new separating device with low cost and high efficiency is in need.

SUMMARY

According to one aspect, there is provided a centrifugation device including a feeding tube defining a longitudinal axis, a plurality of centrifugal plates extending longitudinally and radially around the feeding tube and rotatable about the longitudinal axis, and a centrifugation tank. The centrifugal plates may have coarse surfaces coated with one or more layers of polymer material. The centrifugal plates may be flat or curved. The centrifugation tank can be disposed coaxially with the feeding tube and around the centrifugal plates. A sidewall of the tank may be provided with micro filters and/or nano filters.

In one embodiment, the polymer material may include a mixture of polyvinyl chloride and aromatic heterocyclic polyimides. The ratio of polyvinyl chloride and aromatic heterocyclic polyimides can be 1:9. The thickness of the layer of polymer material can be 2-3 micrometer with a micro-hardness of 1000-1200 gf.

In one embodiment, the filter can be a 1-micron stainless steel micro filter. In another embodiment, the filter can be a polyethylene terephthalate nano filter with a pore size of 10 angstrom.

The centrifugation device may further include one or more turbulators mounted at an inlet of the feeding tube, and a reservoir for supplying a mixture to be centrifuged to the turbulators through a reservoir pipe.

In one embodiment, an inner surface of the feeding tube may be coated with a layer of polymer material including a mixture of polyvinyl chloride and aromatic heterocyclic polyimides. The inner surface of the feeding tube may also have an uneven inner surface.

The centrifugation device may further include an outer shell in which the centrifugation tank is disposed, and a container communicated with the outer shell through a pipe.

According to another aspect, there is provided a method for isolation of algal biomass from algae and aqueous mixture. The method may include the steps of:
(a) providing a centrifugation device including:
a feeding tube defining a longitudinal axis;
a plurality of centrifugal plates extending longitudinally and radially around the feeding tube and rotatable about the longitudinal axis, the centrifugal plates having coarse surfaces coated with one or more layers of polymer material; and
a centrifugation tank disposed coaxially with the feeding tube and around the centrifugal plates, a sidewall of the tank being provided with a filter selected from the group consisting of micro filter and nano filter.
(b) feeding algae and aqueous mixture into the centrifugation device through an inlet of the feeding tube; and
(c) spinning the centrifugal plates at a speed of 2500-4000 RPM after the tank is filled up with the mixture so that biomass starts building up on the centrifugal plates due to adhesiveness of the polymer material and centrifugal force, and aqueous medium diffuses out through the filter and biomass suspends on an inner surface of the filter.

The centrifugal plates may be first coated with a layer of polyvinyl chloride, and then with a layer of polymer material including a mixture of polyvinyl chloride and aromatic heterocyclic polyimides by physical vapor deposition technology.

In one embodiment, the coating of the centrifugal plates may include steps of:
(a) inspecting the centrifugal plates for quantity, material and surface condition;
(b) cleaning stainless steel surfaces of the centrifugal plates with multi-stage of ultrasonic cleaning in alkaline baths without using environmentally damaging additives;
(c) placing the centrifugal plates in a degassing vacuum oven to eliminate residues and micro blasting is applied to remove porous surface layer to ensure adhesiveness;
(d) loading the centrifugal plates into a coating system; and
(e) coating the centrifugal plates by physical vapor deposition technology with one or more layers of polymer material, wherein each coating process comprises the steps of pumping down a processing chamber in 10 to 6 mbar, system checking, temperature controlling, ion etching, coating with polymer and cooling down.

According to a further aspect, there is provided a method for extraction of oil from kitchen residue and/or microalgae. The method may include the steps of:
(a) providing a centrifugation device comprising
a feeding tube defining a longitudinal axis, an inner surface of the feeding tube comprising an uneven surface coated with one or more layers of polymer material;
a plurality of centrifugal plates extending longitudinally and radially around the feeding tube and rotatable about the longitudinal axis, the centrifugal plates having coarse surfaces coated with one or more layers of polymer material;
a centrifugation tank being disposed coaxially with the feeding tube and around the centrifugal plates, a sidewall of the tank being provided with a filter selected from the group consisting of micro filter and nano filter; and one or more turbulators mounted at an inlet of the feeding tube.

(b) passing kitchen residue and/or microalgae through the turbulators to turn laminar flow into turbulent flow;

(c) passing the kitchen residue and/or microalgae through the feeding tube to extract oil by shear force from the polymer coated uneven inner surface of the feeding tube;

(d) spinning the centrifugal plates after the tank is filled up with the kitchen residue and/or microalgae so that oil starts building up on the centrifugal plates, and organic and aqueous mixture diffuses out through the filter.

The centrifugal plates and the inner surface of the feeding tube may be first coated with a layer of polyvinyl chloride, and then with a layer of material including a mixture of polyvinyl chloride and aromatic heterocyclic polyimides by physical vapor deposition technology.

The method may further include the step of pretreating the kitchen residue by screening off and crushing bulky kitchen residue by a pressing device before passing the kitchen residue through the turbulators.

In one embodiment, the coating of the centrifugal plates may include the steps of:

(a) inspecting the centrifugal plates for quantity, material and surface condition;

(b) cleaning stainless steel surfaces of the centrifugal plates with multi-stage of ultrasonic cleaning in alkaline baths without using environmentally damaging additives;

(c) placing the centrifugal plates in a degassing vacuum oven to eliminate residues and micro blasting is applied to remove porous surface layer to ensure adhesiveness;

(d) loading the centrifugal plates into a coating system; and (e) coating the centrifugal plates by physical vapor deposition technology with one or more layers of polymer material, wherein each coating process comprises the steps of pumping down a processing chamber in 10 to 6 mbar, system checking, temperature controlling, ion etching, coating with polymer and cooling down.

Although the centrifugation device is shown and described with respect to certain embodiments, it is obvious that equivalents and modifications will occur to others skilled in the art upon the reading and understanding of the specification. The centrifugation device in the present application includes all such equivalents and modifications, and is limited only by the scope of the claims.

BRIEF DESCRIPTION OF THE DRAWINGS

Specific embodiments of the centrifugation device will now be described by way of example with reference to the accompanying drawings wherein.

DETAILED DESCRIPTION

Reference will now be made in detail to a preferred embodiment of the centrifugation device, examples of which are also provided in the following description. Exemplary embodiments of the centrifugation device are described in detail, although it will be apparent to those skilled in the relevant art that some features that are not particularly important to an understanding of the centrifugation device may not be shown for the sake of clarity.

Furthermore, it should be understood that the centrifugation device is not limited to the precise embodiments described below and that various changes and modifications thereof may be effected by one skilled in the art without departing from the spirit or scope of the protection. For example, elements and/or features of different illustrative embodiments may be combined with each other and/or substituted for each other within the scope of this disclosure and appended claims.

In addition, improvements and modifications which may become apparent to persons of ordinary skill in the art after reading this disclosure, the drawings, and the appended claims are deemed within the spirit and scope of the protection.

It should be noted that throughout the specification and claims herein, when one element is said to be "coupled" or "connected" to another, this does not necessarily mean that one element is fastened, secured, or otherwise attached to another element. Instead, the term "coupled" or "connected" means that one element is either connected directly or indirectly to another element or is in mechanical or electrical communication with another element.

Figure 1A:
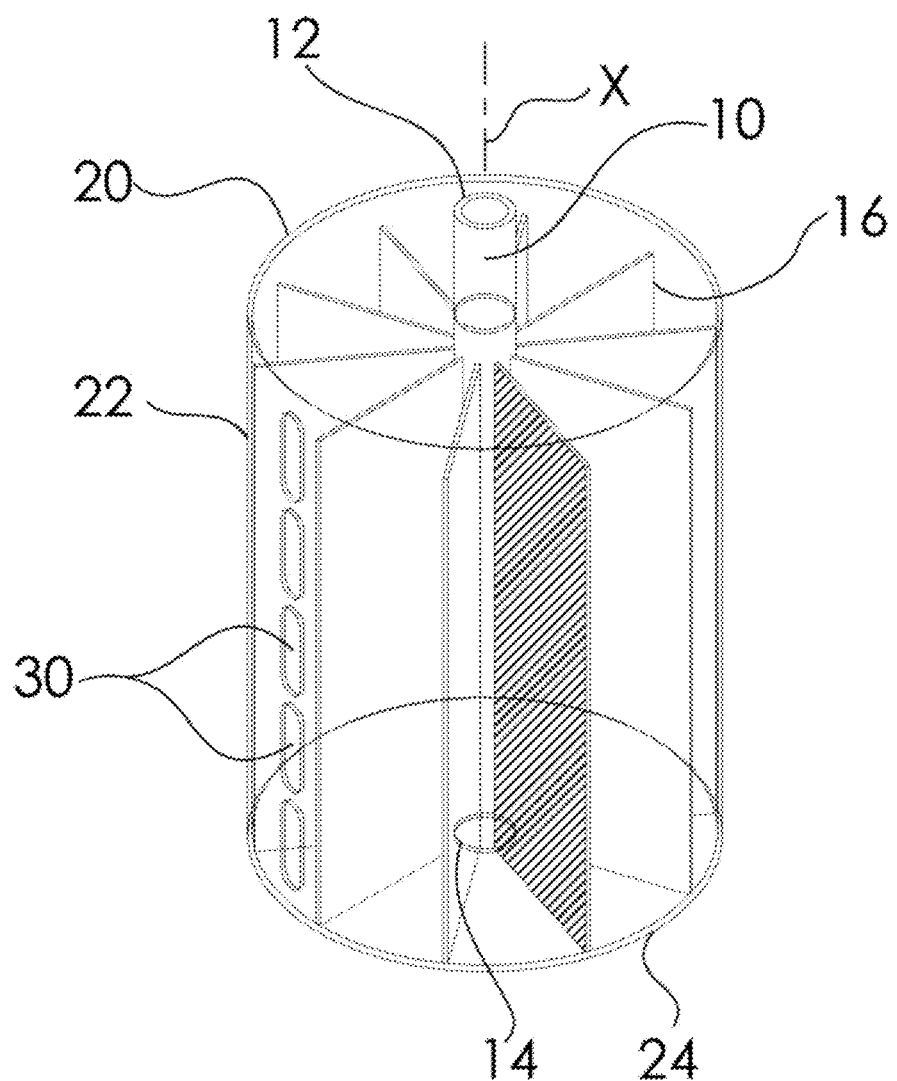
FIG. 1a is a perspective view of a centrifugation device with flat centrifugal plates for isolation of algal biomass from an algae and aqueous mixture according to an embodiment of the present application.
Figure 1B:
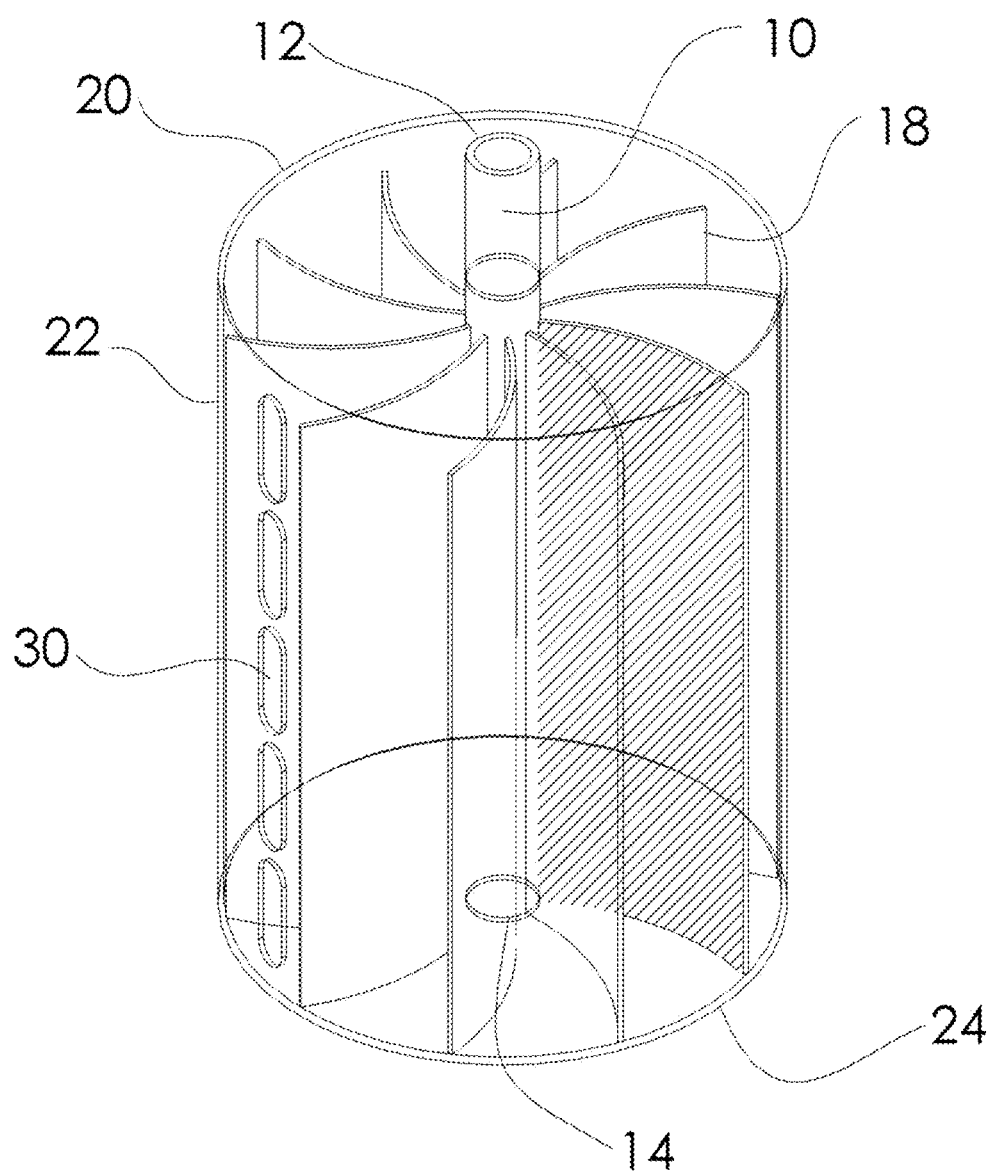
FIG. 1b is a perspective view of a centrifugation device with curved centrifugal plates for isolation of algal biomass from an algae and aqueous mixture according to an embodiment of the present application.

FIGS. 1a and 1b show a centrifugation device with flat/curved centrifugal plates for isolation of algal biomass from an algae and aqueous mixture according to an embodiment of the present application The centrifugation device may include a feeding tube 10 having an inlet 12 and an outlet 14, and defining a longitudinal axis X.

A plurality of centrifugal plates 16, 18 may extend longitudinally and radially around the feeding tube 10 and rotatable about the longitudinal axis X. According to the illustrated embodiment, there are ten centrifugal plates 16, 18, although the number of centrifugal plates 16, 18 may be more or less than 10. The centrifugal plates may be flat as shown in FIG. 1a, or curved as shown in FIG. 1b. It is understood by one skilled in the art that the centrifugal plates may be in any other possible shape.

The centrifugal plates 16, 18 may have coarse surfaces and may be coated with one or more layers of polymer material adapted to suspend thereon algal biomass during centrifugation. The polymer material may include a mixture of polyvinyl chloride and aromatic heterocyclic polyimides. The thickness of the layer of polymer material may be 2-3 micrometer with a micro-hardness of 1000-1200 gf. Of course, it is contemplated by one skilled in the art the centrifugal plates 16, 18 may be coated with other suitable polymer material that is able to suspend algal biomass during centrifugation.

The centrifugation device may further include a centrifugation tank 20 having a sidewall 22 and a bottom wall 24. The tank 20 may be cylindrical in shape, or in other appropriate shape. The tank 20 may be disposed coaxially with the feeding tube 10 and around the centrifugal plates 16, 18. The inlet 12 of the feeding tube 10 may be positioned at an upper end of the tank 20. The outlet 14 of the feeding tube 10 may be positioned above the bottom wall 24 of the tank 20. The sidewall 22 of the tank 20 may be provided with one or more filters 30 through which aqueous medium can diffuse. The filters 30 may be 1-micron stainless steel micro filters, or polyethylene terephthalate nano filters with a pore size of 10 angstrom. Nano filters have better filtration tendency (measure in volumetric) than micro filters, but higher energy consumption might be required.

According to the illustrated embodiment, the sidewall 22 of the tank 20 can be provided with a plurality of oblong filters 30. It is understood that the filters 30 are formed around the entire sidewall 22 of the tank 20 to produce the best result, and that the filters 30 may be in any other appropriate shape such as rectangle, square, circle, etc.

Operation of Centrifugation Device:

Algae and aqueous mixture can be fed into the centrifugation device through the inlet 12 of the feeding tube 10. After the mixture fills up the centrifugation tank, centrifugal plates 16, 18 start spinning to a top speed of 2500-4000 RPM. Biomass starts building up on the surface of the polymer coated centrifugal plates 16, 18 due to adhesiveness of the polymer and centrifugal force. Aqueous medium diffuses out through the micro/nano filters 30 and biomass suspends on the surfaces of filters 30 inside the centrifugation tank 20. Microalgae paste (biomass) can be harvested after centrifugation. Most of the aqueous medium diffuses through the micro/nano filters 30, depending on the rotational speed and duration of centrifugation.

This method of separating algal biomass from aqueous medium, utilizing micro/nano filter, centrifugal force and adhesiveness property of polymer coating can reduce the separation energy from the normal 25 MJ/kg to below 1.9 MJ/kg. Thus, algal based fuel has full potential to become first class regenerative fuel when this technology is extensively adapted.

Figure 2A:
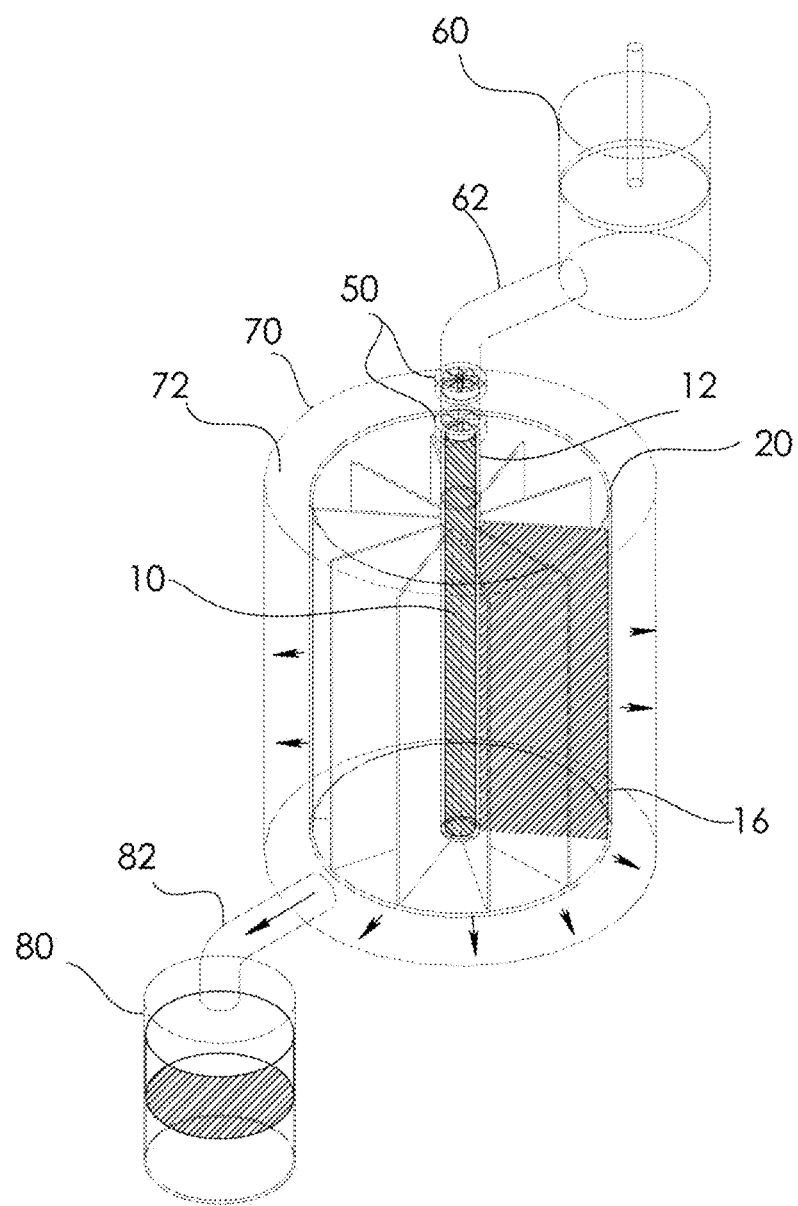
FIG. 2a is a perspective view of a centrifugation device with flat centrifugal plates for extraction of oil from kitchen residue and/or microalgae according to an embodiment of the present application.
Figure 2B:
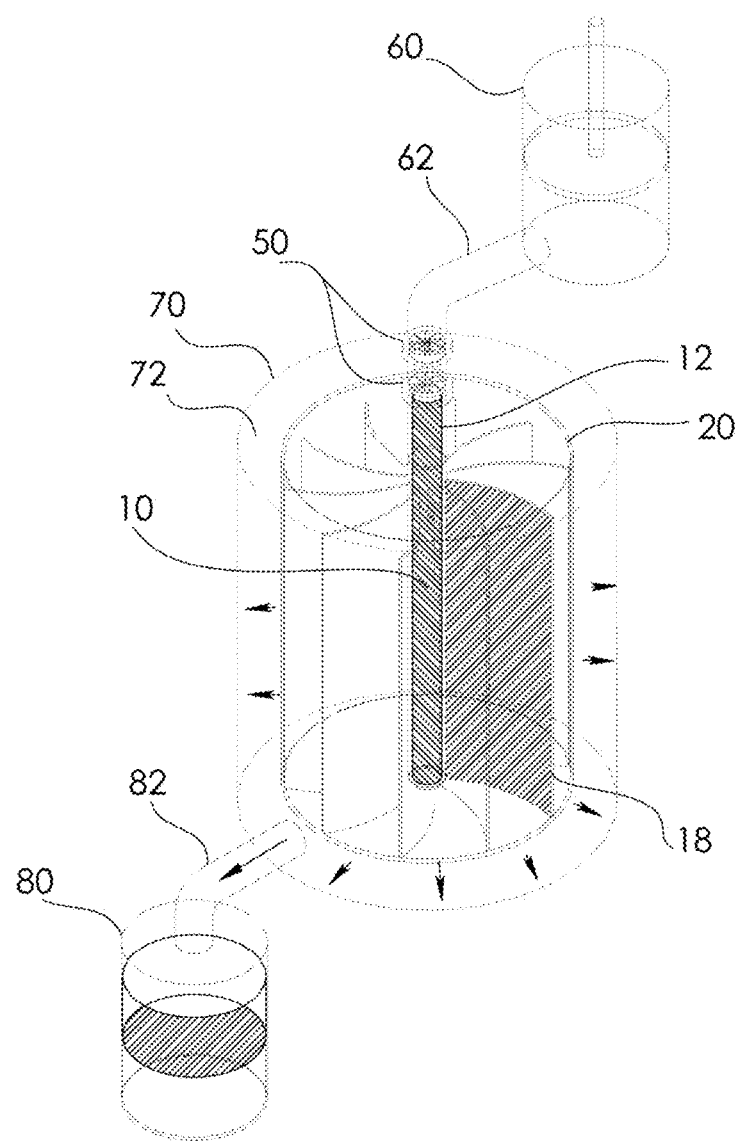
FIG. 2b is a perspective view of a centrifugation device with curved centrifugal plates for extraction of oil from kitchen residue and/or microalgae according to an embodiment of the present application.

FIGS. 2a and 2b show a centrifugation device with flat/curved centrifugal plates for extraction of oil from kitchen residue and/or microalgae according to an embodiment of the present application.

Similar to the previous embodiment, the centrifugation device may include a feeding tube 10 having an inlet 12 and an outlet 14, and defining a longitudinal axis X.

A plurality of centrifugal plates 16, 18 may extend longitudinally and radially around the feeding tube 10 and rotatable about the longitudinal axis X. According to the illustrated embodiment, there are ten centrifugal plates 16, 18, although the number of centrifugal plates 16, 18 may be more or less than 10. The centrifugal plates may be flat as shown in FIG. 1a, or curved as shown in FIG. 1b. It is understood by one skilled in the art that the centrifugal plates may be in any other possible shape.

The centrifugal plates 16, 18 may have coarse surfaces and may be coated with one or more layers of polymer material adapted to suspend thereon organic matter during centrifugation. The polymer material may include a mixture of polyvinyl chloride and aromatic heterocyclic polyimides.

The thickness of the layer of polymer material may be 2-3 micrometer with a micro-hardness of 1000-1200 gf. Of course, it is contemplated by one skilled in the art the centrifugal plates 16, 18 may be coated with other suitable polymer material that is able to suspend organic matter during centrifugation.

The centrifugation device may further include a centrifugation tank 20 having a sidewall 22 and a bottom wall 24. The tank 20 may be cylindrical in shape, or in other appropriate shape. The tank 20 may be disposed coaxially with the feeding tube 10 and around the centrifugal plates 16, 18. The inlet 12 of the feeding tube 10 may be positioned at an upper end of the tank 20. The outlet 14 of the feeding tube 10 may be positioned above the bottom wall 24 of the tank 20. The sidewall 22 of the tank 20 may be provided with one or more filters 30 through which aqueous and organic mixture can diffuse. The filters 30 may be 1-micron stainless steel micro filters, or polyethylene terephthalate nano filters with a pore size of 10 angstrom.

According to the illustrated embodiment, the sidewall 22 of the tank 20 can be provided with a plurality of oblong filters 30. It is understood that the filters 30 are formed around the entire sidewall 22 of the tank 20 to produce the best result, and that the filters 30 may be in any other appropriate shape such as rectangle, square, circle, etc.

The centrifugation device may further include a series of turbulators 50 mounted at the inlet 12 of the feeding tube 10 to enhance laminar flow. According to the illustrated embodiment, there are two turbulators 50, though the number of turbulator may be more or less than two.

The centrifugation device may further include a reservoir 60 for supplying kitchen residue to the turbulators 50 through a reservoir pipe 62.

Figure 9A:
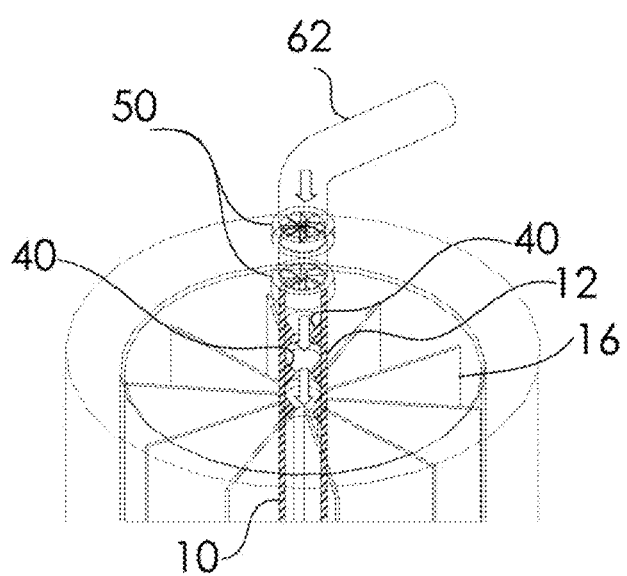
FIG. 9a is a perspective view of two turbulators and a feeding pipe with a rough surface designed for direct flow according to an embodiment of the present application.
Figure 9B:
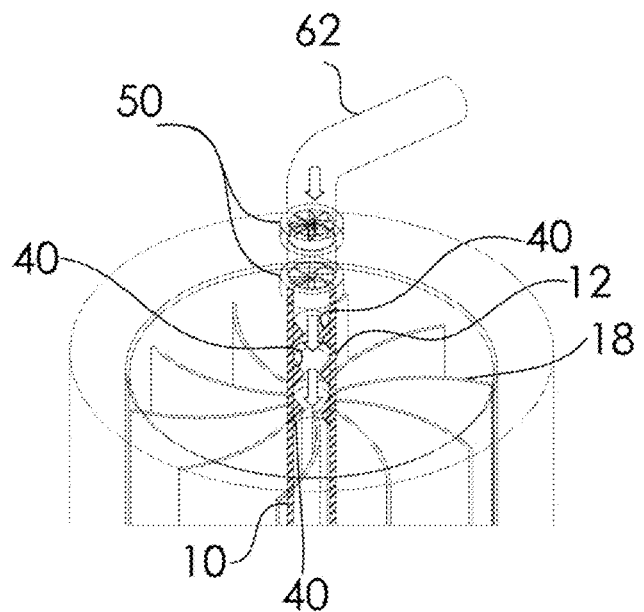
FIG. 9b is a perspective view of two turbulators and a feeding pipe with a rough surface designed for direct flow according to another embodiment of the present application.
Figure 10:
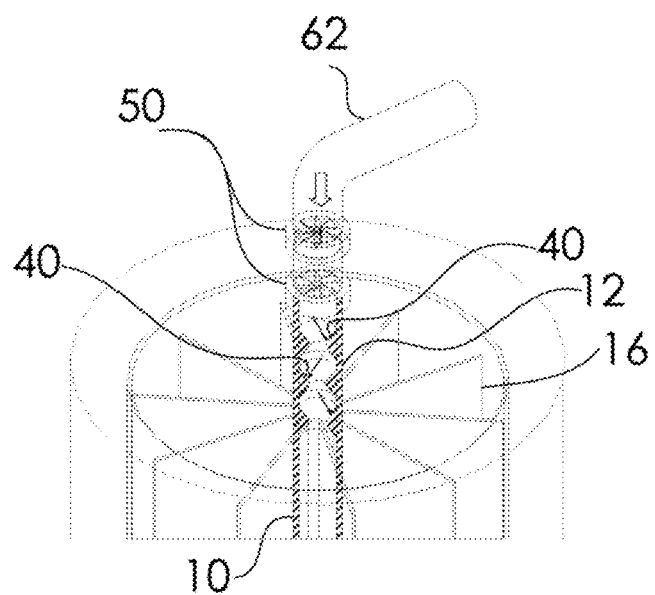
FIG. 10 is a perspective view of two turbulators and a feeding pipe with a rough surface designed for redirected flow according to an embodiment of the present application.

An inner surface of the feeding tube 10 may be coated with one or more layers of polymer material. For example, the inner surface of the feeding tube 10 may be coated with a layer of polymer material including polyvinyl chloride or a mixture of polyvinyl chloride and aromatic heterocyclic polyimides. The inner surface of the feeding tube 10 may have an uneven inner surface. The uneven inner surface may by formed by a plurality of protrusions 40 (FIGS. 9 and 10).

The centrifugation device may further include an outer shell 70 in which the centrifugation tank 20 is disposed. The outer shell 70 and the tank 20 can define a receptacle 72 for receiving oil and water diffused through the filters 30.

The centrifugation device may further include a container 80 for containing oil and water from the receptacle 72 through a drainage pipe 82.

Operation of Centrifugation Device:

The kitchen residue and/or microalgae to be centrifuged can be stored in the reservoir 60. The kitchen residue and/or microalgae may go through the series of turbulators 50 into the feeding tube 10. The laminar flow of the kitchen residue and/or microalgae can be enhanced into a turbulent flow by the series of turbulators 50. Organic matter in the medium will be extracted as oil by sheer force from the polymer coated uneven inner surface of the feeding tube 10. After the kitchen residue and/or microalgae fills up the centrifugation tank 20, centrifugal plates 16, 18 spin at a relatively low rotational force. Organic matter starts building up on the surface of the centrifugal plates 16, 18 due to adhesiveness of the polymer coating and centrifugal force, and lyses into smaller oil. Aqueous and organic mixture diffuses through the filters 30 and is collected in the container 80. Organic matter (oil) can be harvested after the mixture is stabilized.

Kitchen residue may be pretreated by screening off or crushing bulky residue. To increase fluidity of the kitchen residue, it may go through a pressing device before entering the reservoir 60 and the series of turbulators 50. Microalgae medium can be fed into the reservoir 60 directly.

Figure 3:
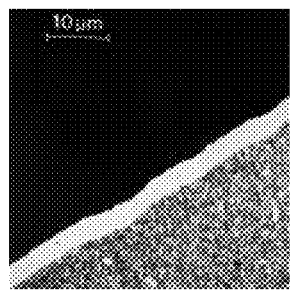
FIG. 3 is a magnified image showing the thickness of the coating for each polymer layer.

Coating Nature of the Centrifugal Plates:

In order to ensure the adhesiveness from polymer mixture coating while maintaining the sharpness and roughness of the surface simultaneously, an extremely thin coating technology is required. Adapting the method of physical vapor deposition (PVD), a single layer of polymer is merely a few thousandth of millimeter thick but sturdy like steel. Multiple polymer layers on the stainless steel surface can tolerate abrasive wear from long term chemical and physical contact. As shown in FIG. 3, an ideal thickness of the coating is about 2 to 3 micrometer for each polymer layer with a microhardness of 1000 to 1200 gf.

Figure 4:
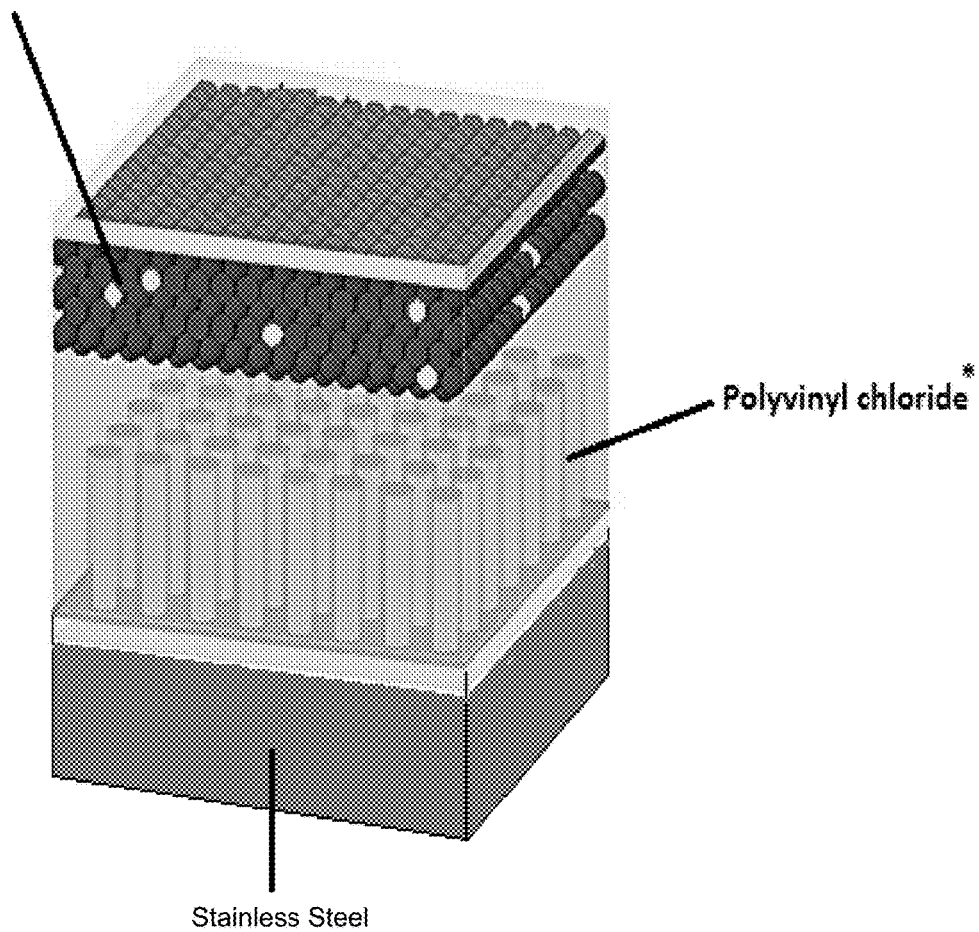
FIG. 4 is an illustrative diagram showing the coatings of a stainless steel centrifugal plates according to an embodiment of the present application.

As shown in FIG. 4, coating procedure of the centrifugal plates includes:

Inspection: Part to be coated is checked for quantity, material and surface condition.

Cleaning: Cleaning is a crucial step for coating adhesion. Stainless steel surface of the part is cleaned with multi-stage of ultrasonic cleaning in alkaline baths without environmentally damaging additives.

Pretreatment: The part is placed in a degassing vacuum oven to eliminate residues and micro blasting is applied to remove porous surface layer to ensure adhesiveness.

Loading: Ensure substrate holders are inserted into the coating system. Define arrangement with reproducible precision.

Coating: The part may be coated by PVD technology with two layers of different polymer materials to ensure the adhesiveness and durability. Each coating process goes through the following procedure: Pump down a processing chamber in 10 to 6 mbar, system check, temperature control for required temperature, ion etch for clean surfaces, coating with desire polymer, cool down.

Coating sequences: Polyvinyl chloride which acts as a primer on the stainless steel surface, then 1:9 Polyvinyl chloride/Aromatic heterocyclic polyimides.

Figure 5:
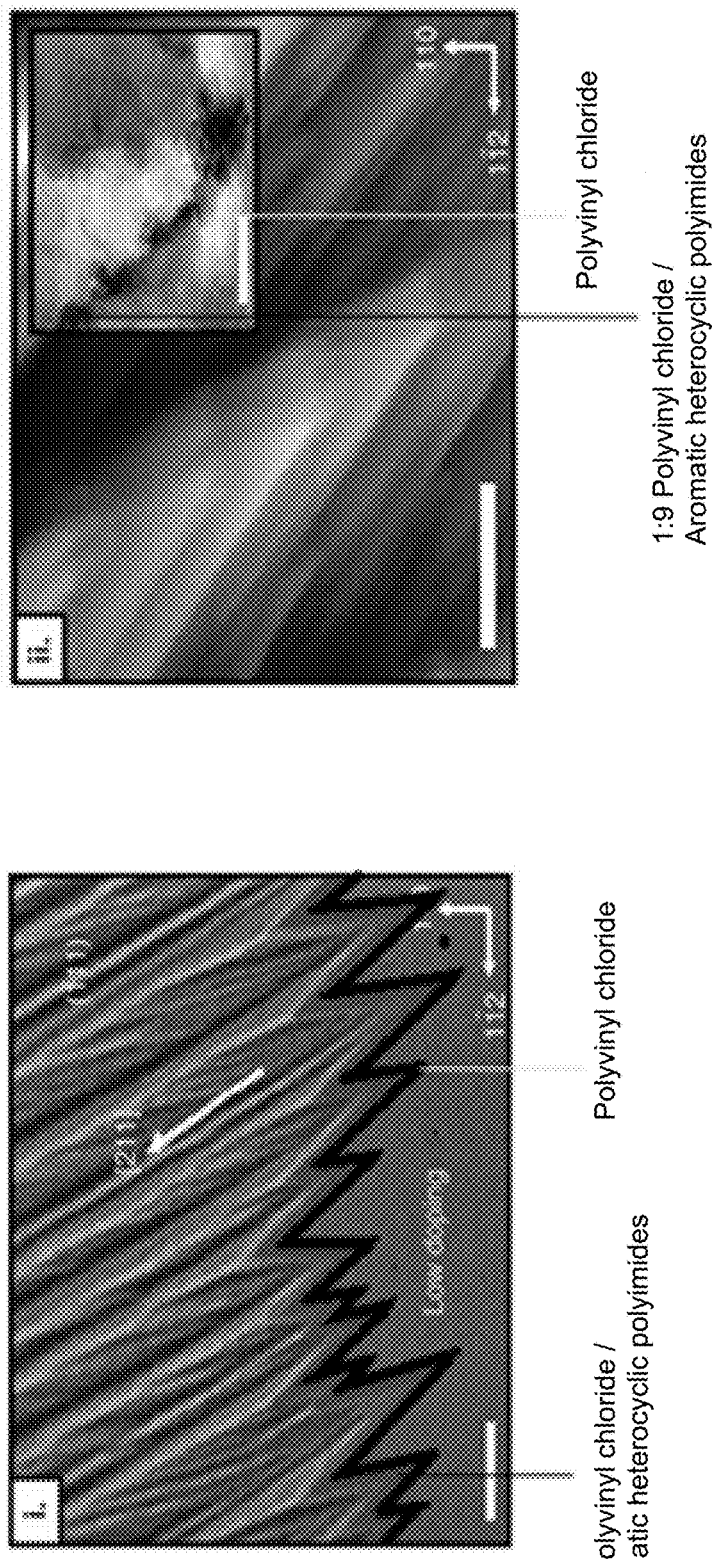
FIG. 5 shows magnified images (×1000 and ×1200) showing the polymer coating on a stainless steel centrifugal plate.

Polymer Mixture Adhesiveness Nature:

FIG. 5 shows a magnified image of the polymer coating on the stainless steel centrifugal plate 16, 18. 1:9 Polyvinyl chloride/aromatic heterocyclic polyimides mixture can indulge the best adhesive coated surface to suspend algal biomass during centrifugation. Due to the adhesive nature of the polymer, lower RPM is required to complete the centrifugation, and thus much lower energy can be consumed comparing to general method of dewatering.

Figure 6:
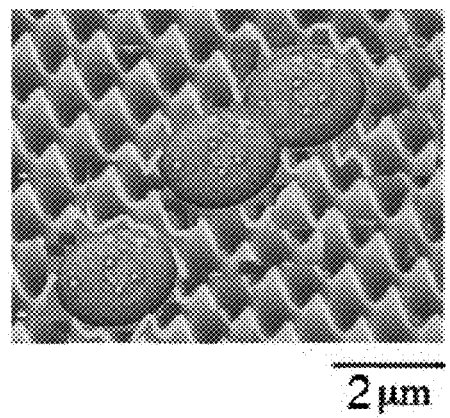
FIG. 6 is a magnified image showing the suspension of microalgae on an adhesive surface of the polymer coating on the stainless steel centrifugal plate.

As shown in FIG. 6, since algal strain produces hydrocarbons, microalgae (such as *Botryococcus Braunii*) can suspend on the adhesive surface of the polymer coating.

Figure 7:
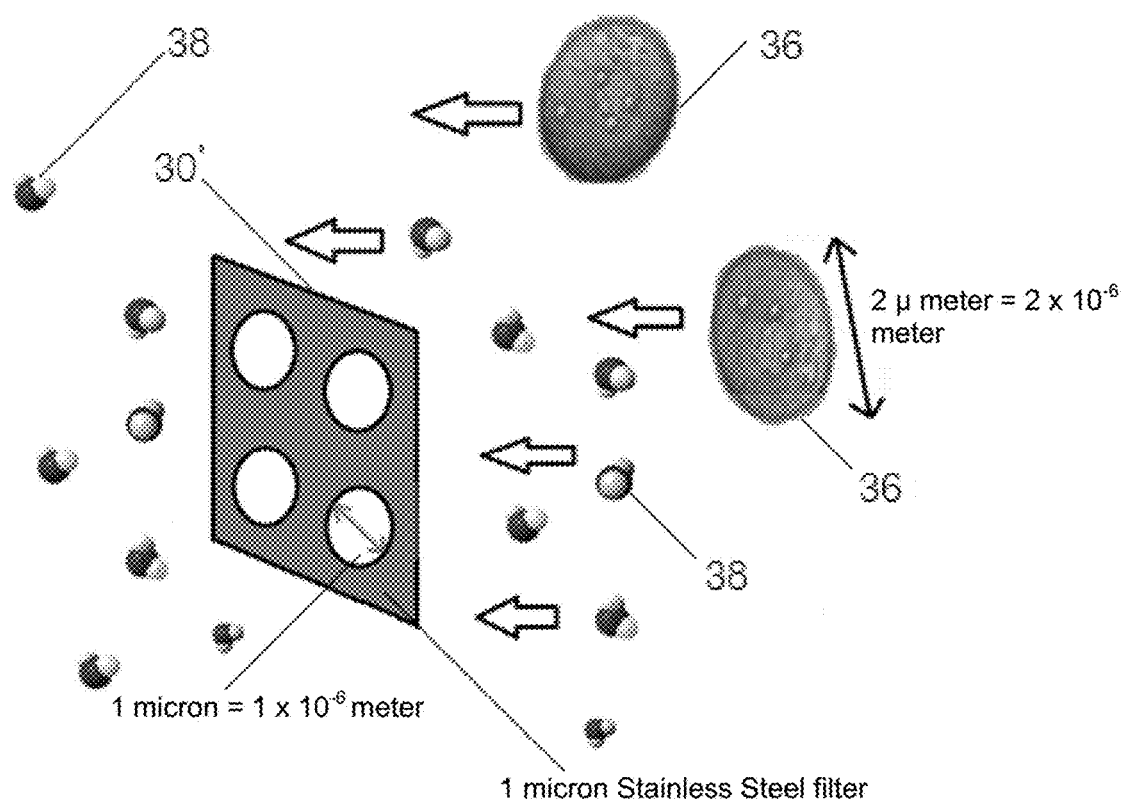
FIG. 7 is an illustrative diagram showing pressure generated by centrifugation (pressure represented in vectors) pushes particles of aqueous and algal biomass mixture onto a 1-micro stainless steel filter.
Figure 8:
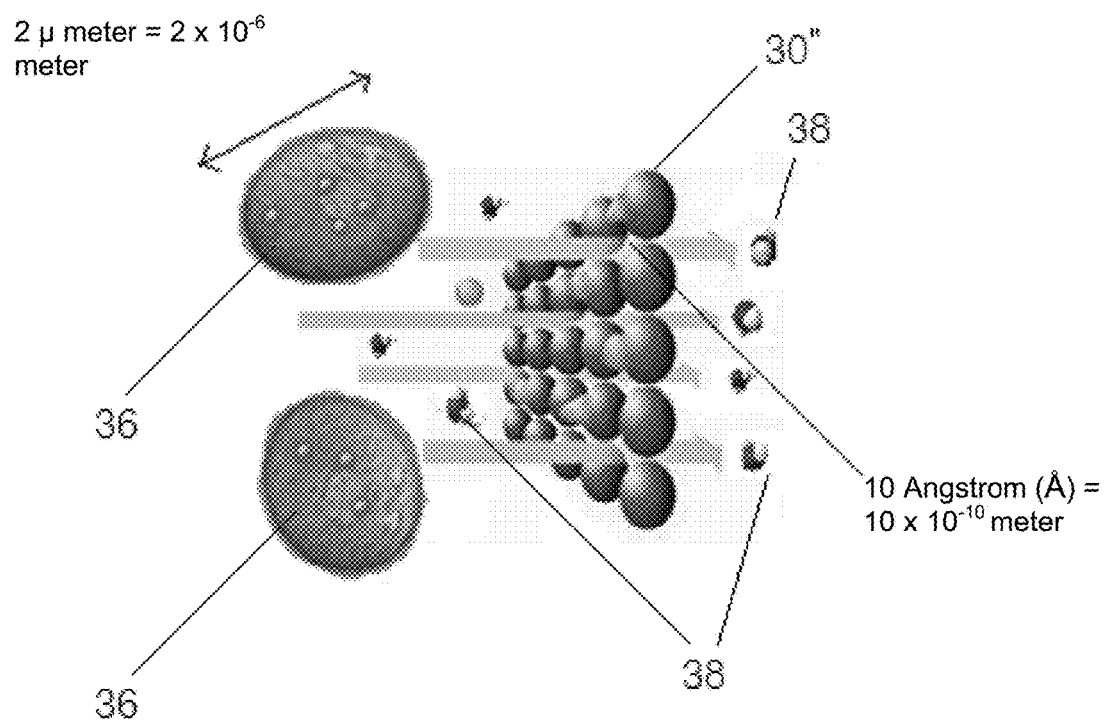
FIG. 8 is an illustrative diagram showing pressure generated by centrifugation (pressure represented in vectors) pushes particles of aqueous and algal biomass mixture onto a nano filter.

Micro/Nano Filtration:

As illustrated in FIGS. 7 and 8, pressure (represented by vectors) generated by centrifugation pushes particles of aqueous and algal biomass mixture onto the 1-micron stainless steel micro filters 30' (FIG. 7), or the polyethylene terephthalate nano filters with a pore size of 10 angstrom 30" (FIG. 8). Only water molecules 38 are small enough to pass through the pores of the micro/nano filters 30', 30". Microalgae 36, such as *Botryococcus Braunii*, will be suspended on the inner surfaces of the micro/nano filters 30', 30". The objective of one-step dewatering can be achieved.

Turbulators and Polymer Coating:

Combination of turbulators 50 and adhesive nature of polymer coating can give a new direction of recycle idea. The series of turbulators 50 can turn a laminar flow into a turbulent flow, which creates a very powerful vortex. Such vortex accelerates the medium passing through the feeding tube 10 to a very high angular velocity, generating a very strong force. This force presses the kitchen residue and/or microalgae against the adhesive rough surface of the centrifugal plates 16, 18. The organic matter will be shredded as a result. A new design of blockage inside of the feeding tube 10 can result in better rupture. FIGS. 9a and 9b show the shortest route that the flow will pass through. The arrows in FIG. 10 show a zig-zag shaped redirected route when the flow passes through the feeding tube 10. This redirected route can provide additional collision, which ultimately gives a better result. The zig-zag shaped redirected route may be formed by the protrusions 40 formed on the inner surface of the feeding tube 10.

Figure 11A:
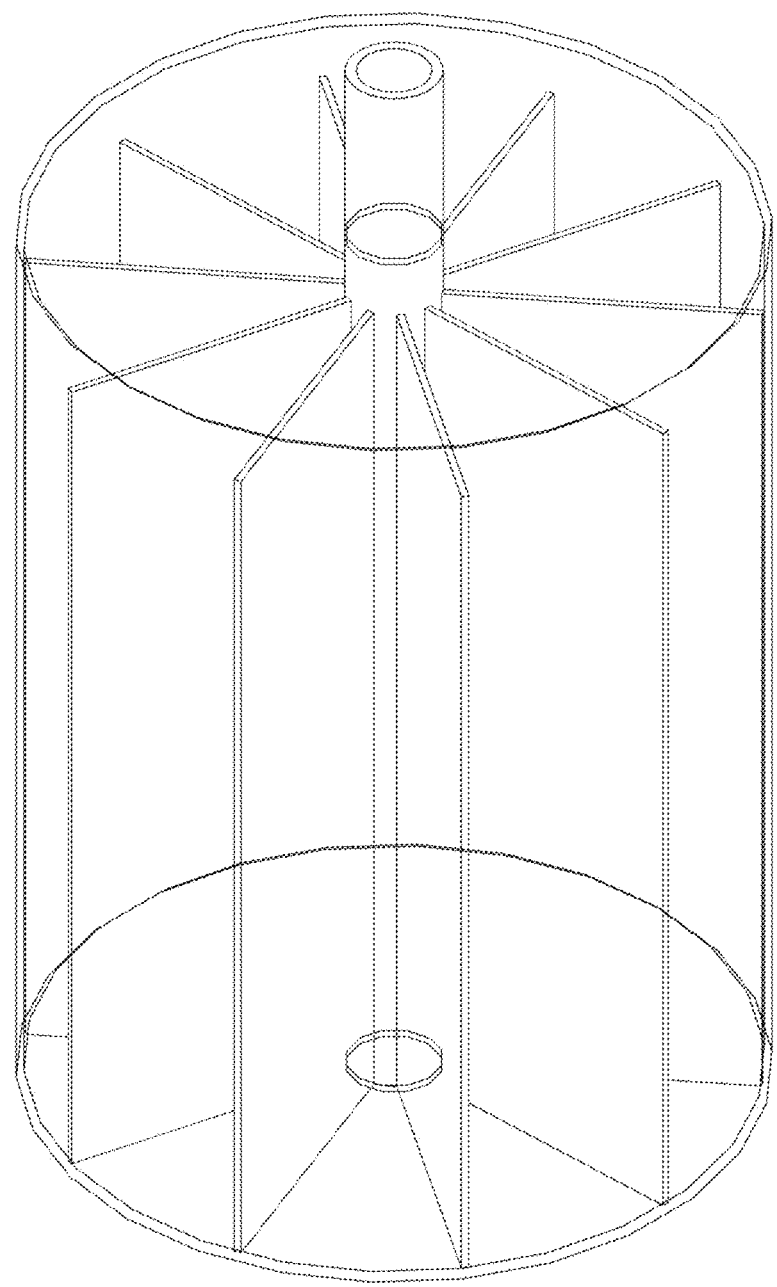
FIG. 11a is a perspective view of the centrifugation device of the prior art with flat centrifugal plates and a centrifugation tank without filters.
Figure 11B:
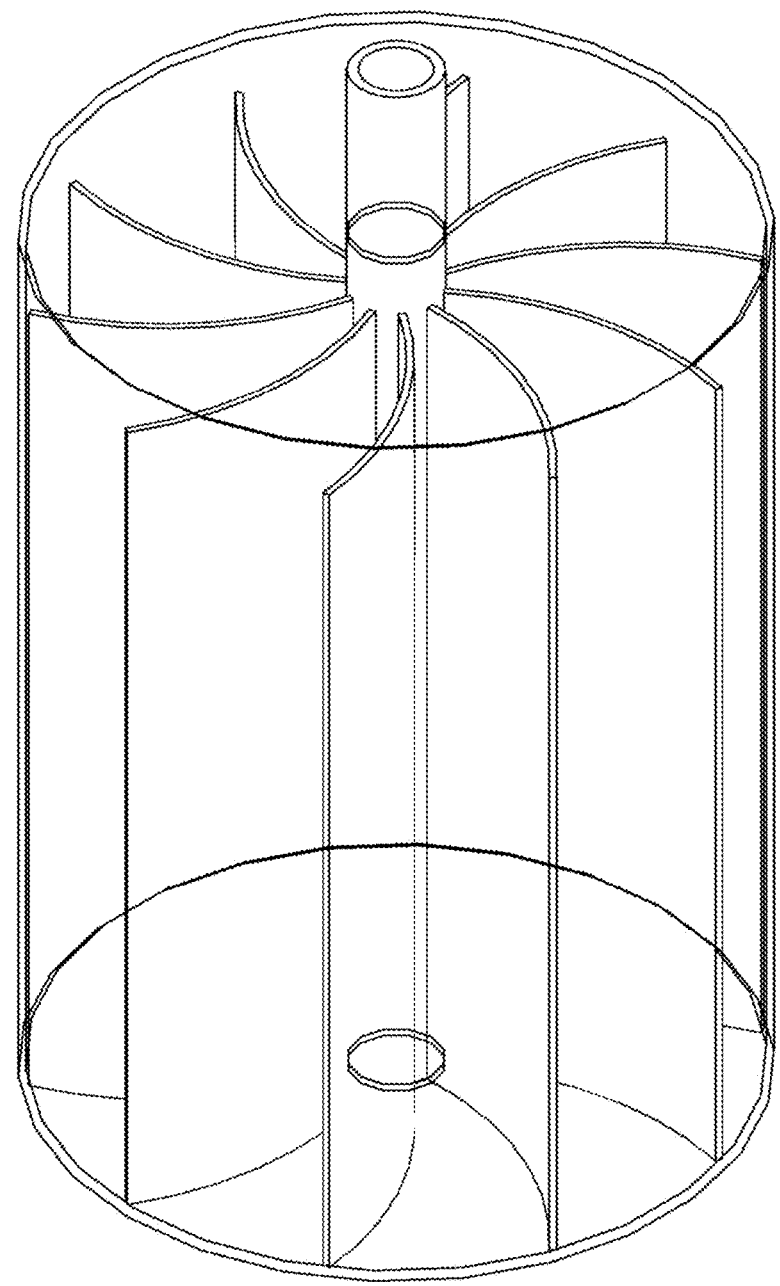
FIG. 11b is a perspective view of the centrifugation device of the prior art with curved centrifugal plates and a centrifugation tank without filters.

Referring to the prior art in FIGS. 11a and 11b, the centrifugation tank has no built-in filter. Additional aqueous draining stage is required before harvesting biomass.

Figure 12A:
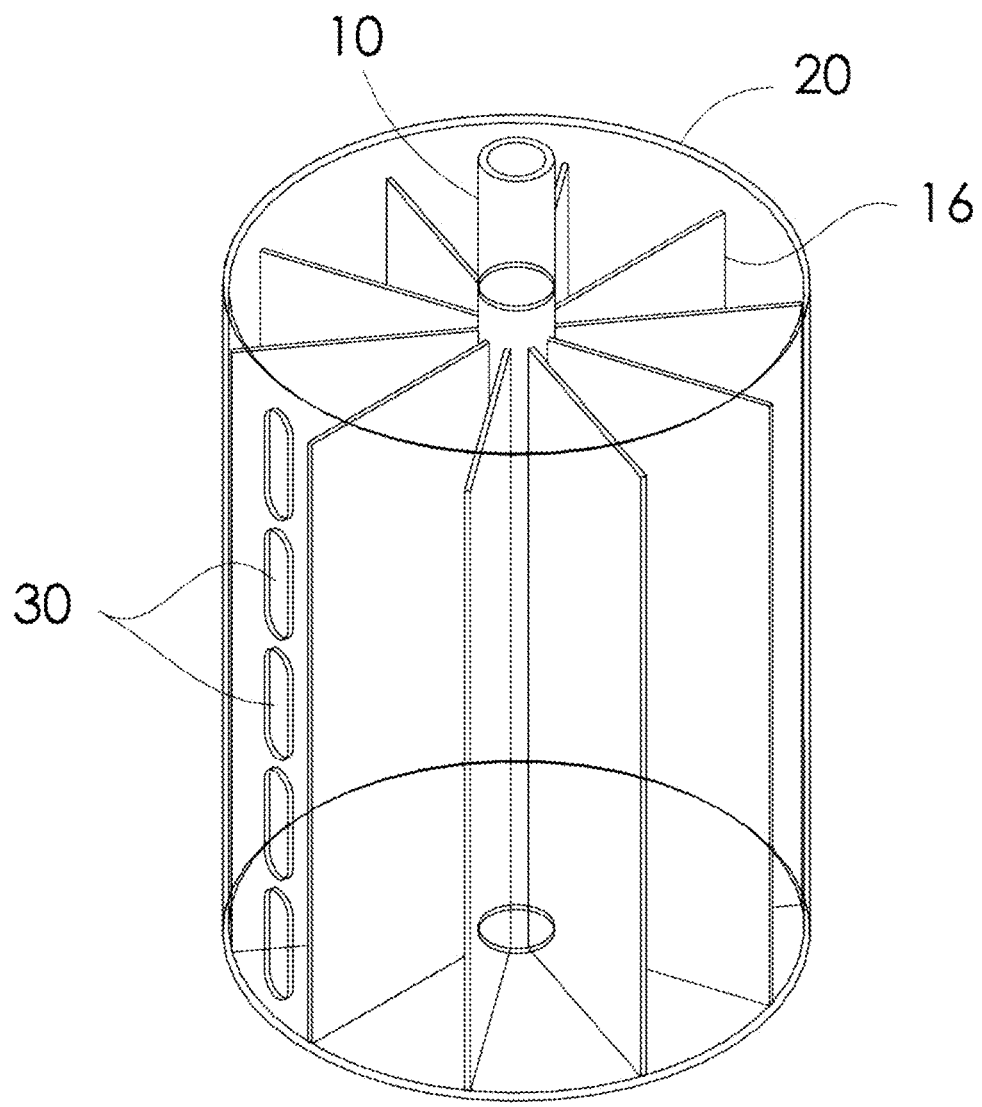
FIG. 12a is a perspective view of the centrifugation device with flat centrifugal plates and a centrifugation tank with 1-micron stainless steel filters according to an embodiment of the present application.
Figure 12B:
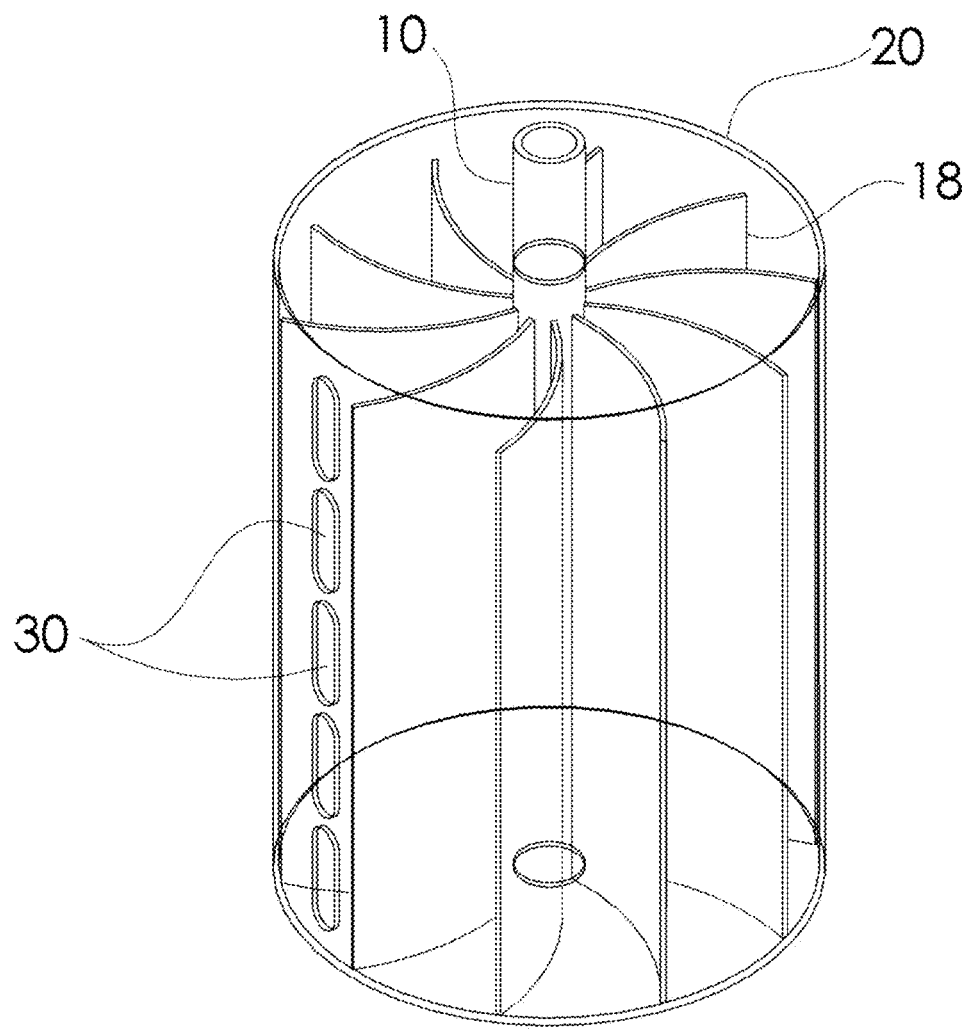
FIG. 12b is a perspective view of the centrifugation device with curved centrifugal plates and a centrifugation tank with 1-micron stainless steel filters according to an embodiment of the present application.

As shown in FIGS. 12a and 12b, aqueous medium can drain/diffuse out of the micro/nano filters 30', 30" of the centrifugation device of the present application during centrifugation. Biomass can be harvested in one single step.

Figure 13A:
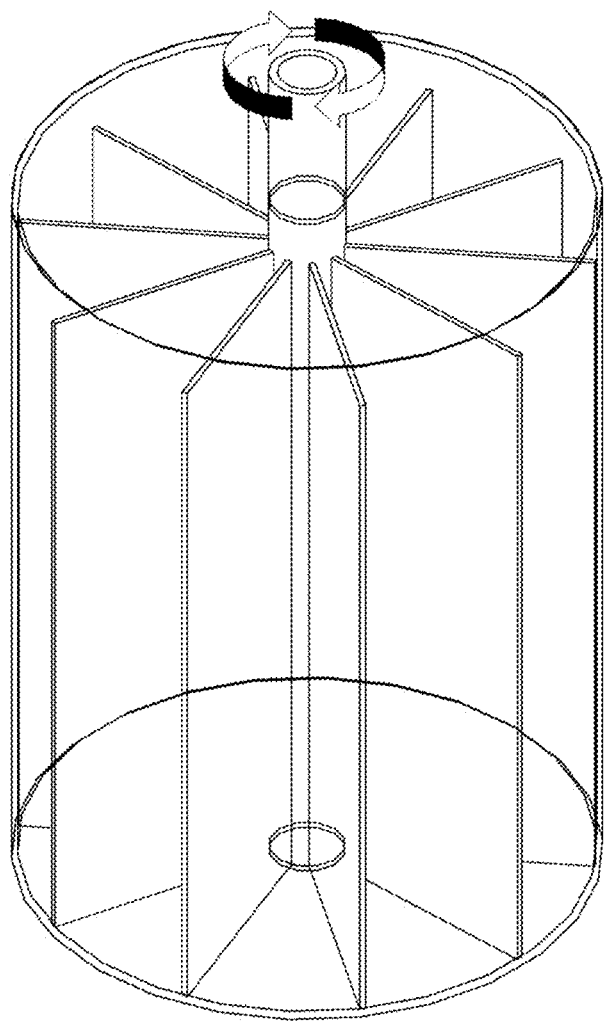
FIG. 13a is a perspective view of the centrifugation device of the prior art with no polyimide coating on the flat centrifugal plates.
Figure 13B:
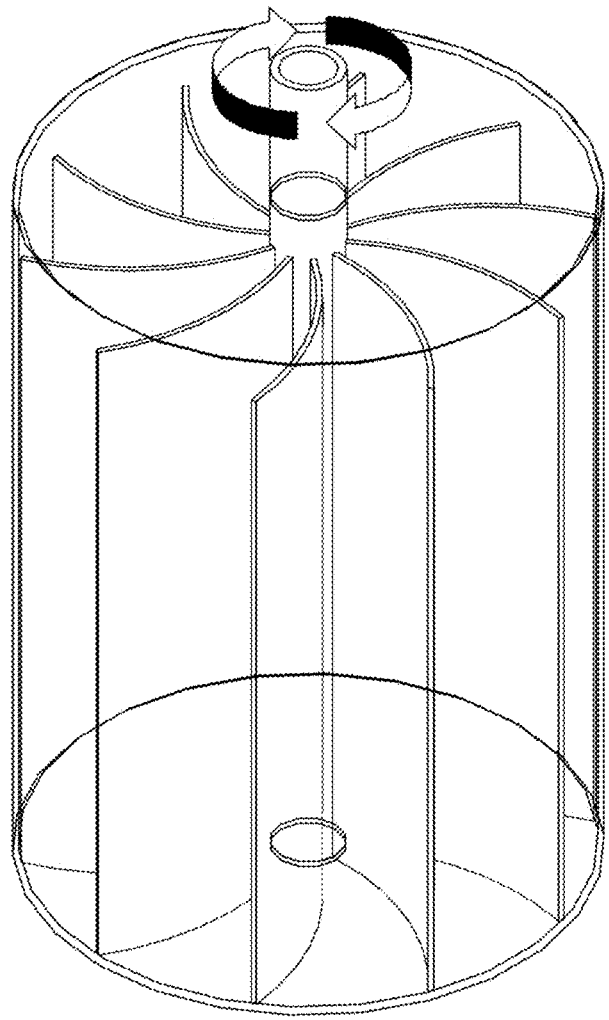
FIG. 13b is a perspective view of the centrifugation device of the prior art with no polyimide coating on the curved centrifugal plates.

Referring to the prior art in FIGS. 13a and 13b, since the centrifugal plates do not have polyimide coating, biomass cannot suspend on it and hence a higher revolution speed is required to complete the centrifugation which leads to higher energy consumption.

Figure 14A:
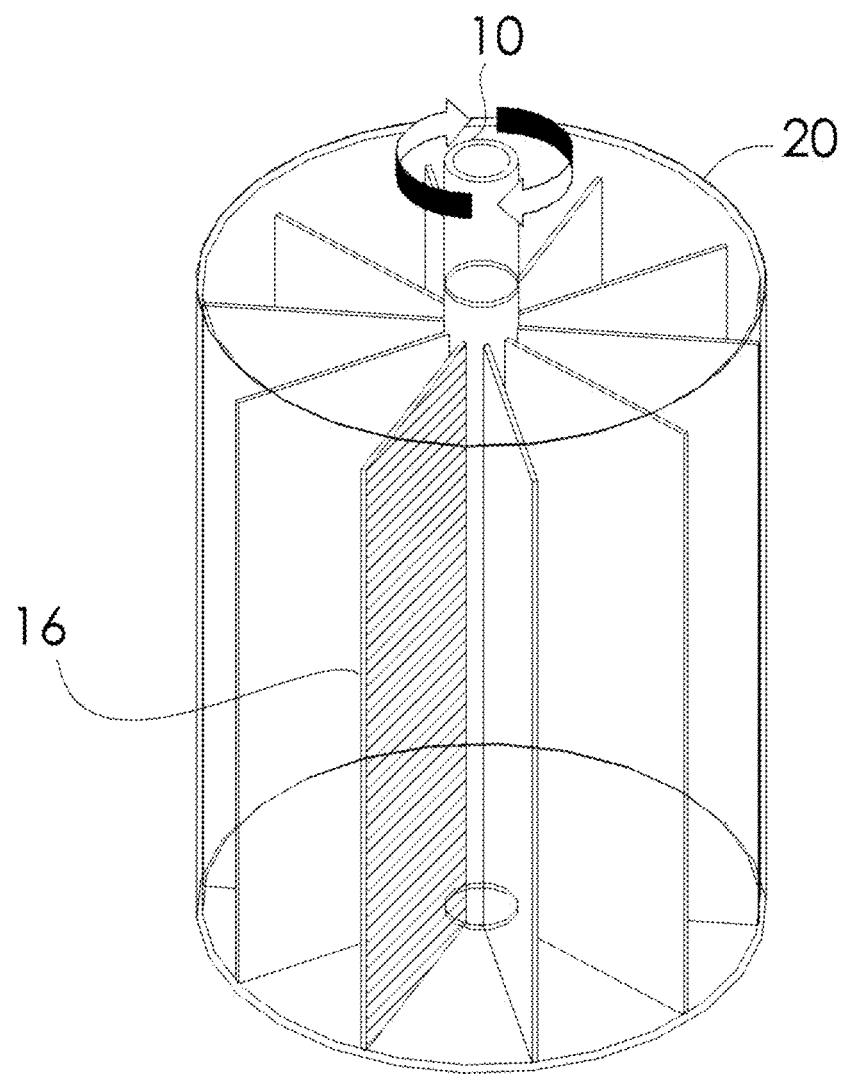
FIG. 14a is a perspective view of the centrifugation device with polyimide coating on the flat centrifugal plates according to an embodiment of the present application.
Figure 14B:
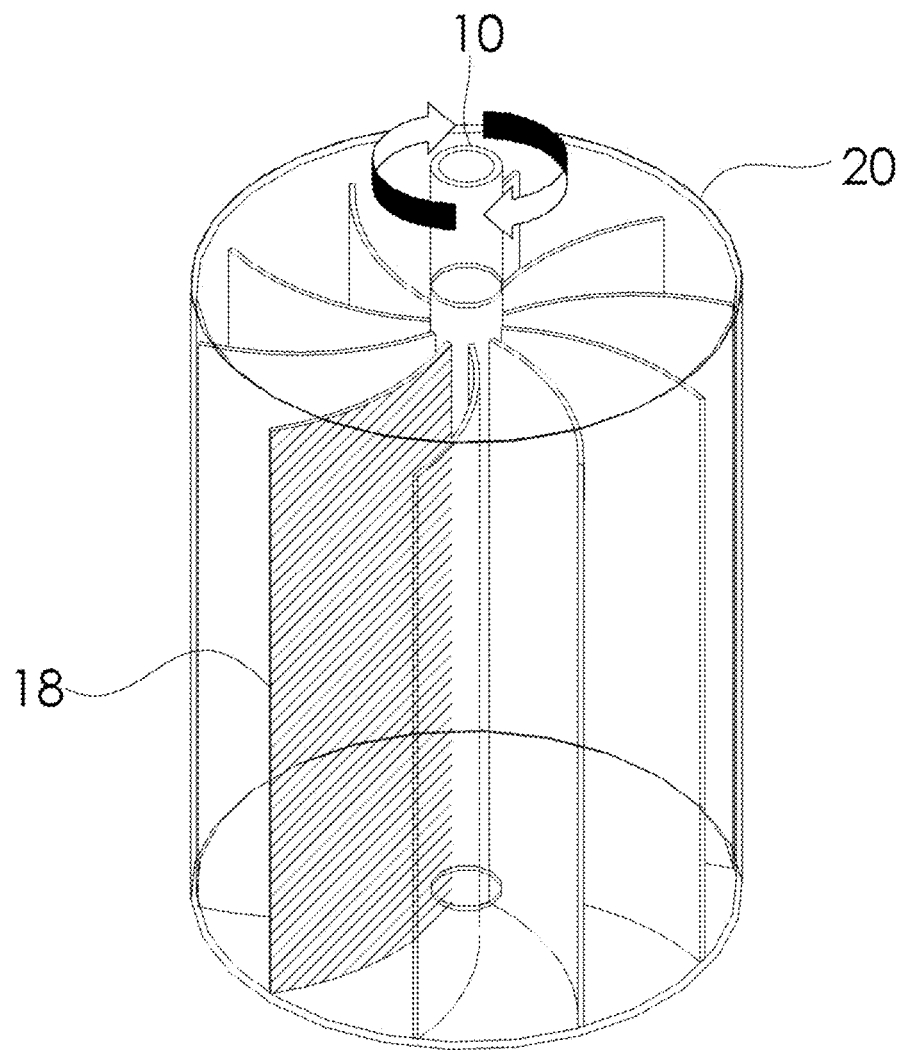
FIG. 14b is a perspective view of the centrifugation device with polyimide coating on the curved centrifugal plates according to an embodiment of the present application.

As illustrated in FIGS. 14a and 14b, the polymer coating on the centrifugal plates 16, 18 of the centrifugation device of the present application enhances adhesiveness to biomass during centrifugation. Lower revolution speed leads to less energy consumption.

Figure 15A:
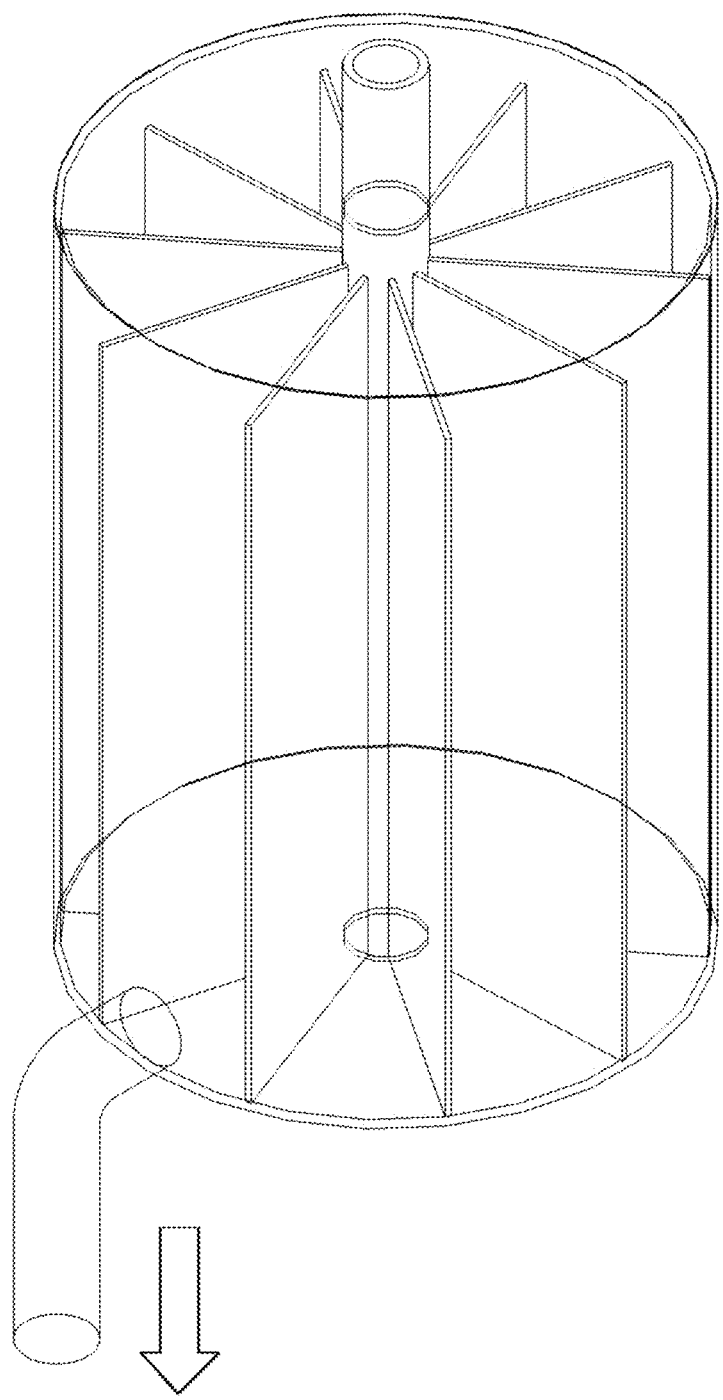
FIG. 15a is a perspective view of the centrifugation device of the prior art with flat centrifugal plates, a centrifugation tank without filters, and an aqueous drainage pipe.
Figure 15B:
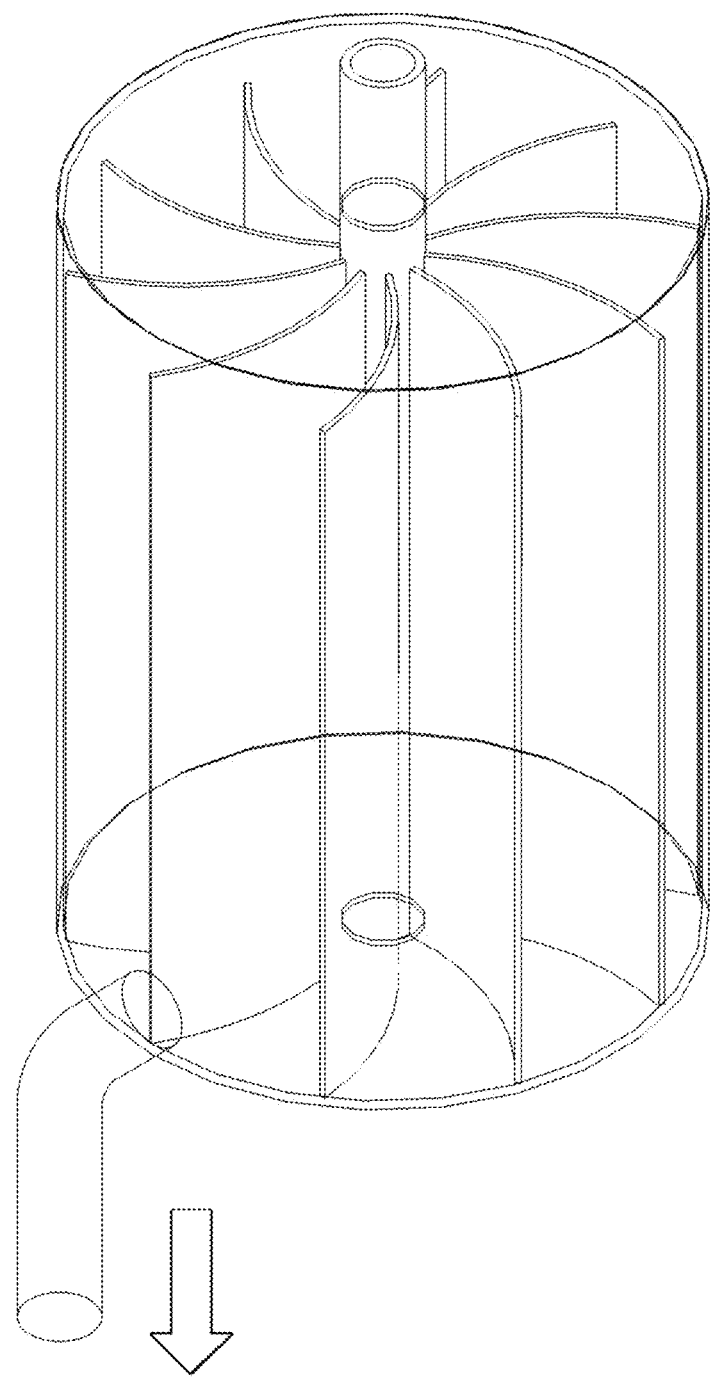
FIG. 15b is a perspective view of the centrifugation device of the prior art with curved centrifugal plates, a centrifugation tank without filters, and an aqueous drainage pipe.

Referring to the prior art in FIGS. 15a and 15b, without the filter, aqueous drainage is required after centrifugation, which often leads to excessive loss of biomass.

Figure 16A:
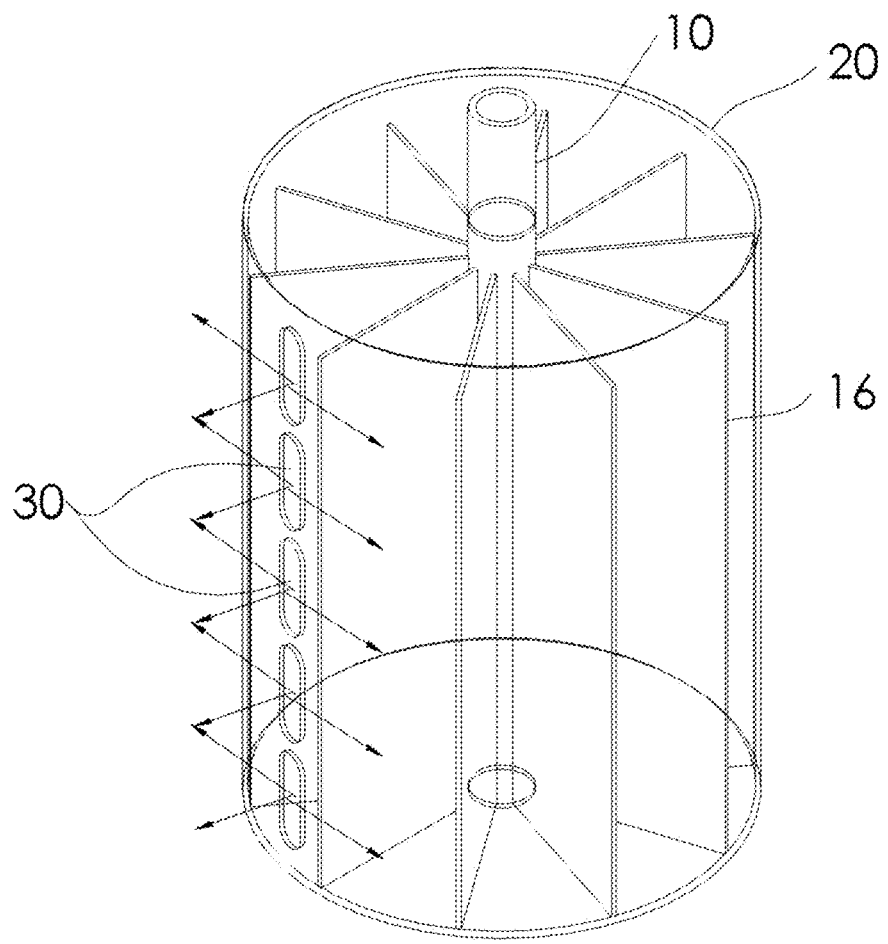
FIG. 16a is a perspective view of the centrifugation device with flat centrifugal plates, a centrifugation tank with 1-micron stainless steel filters, and without an aqueous drainage pipe according to an embodiment of the present application.
Figure 16B:
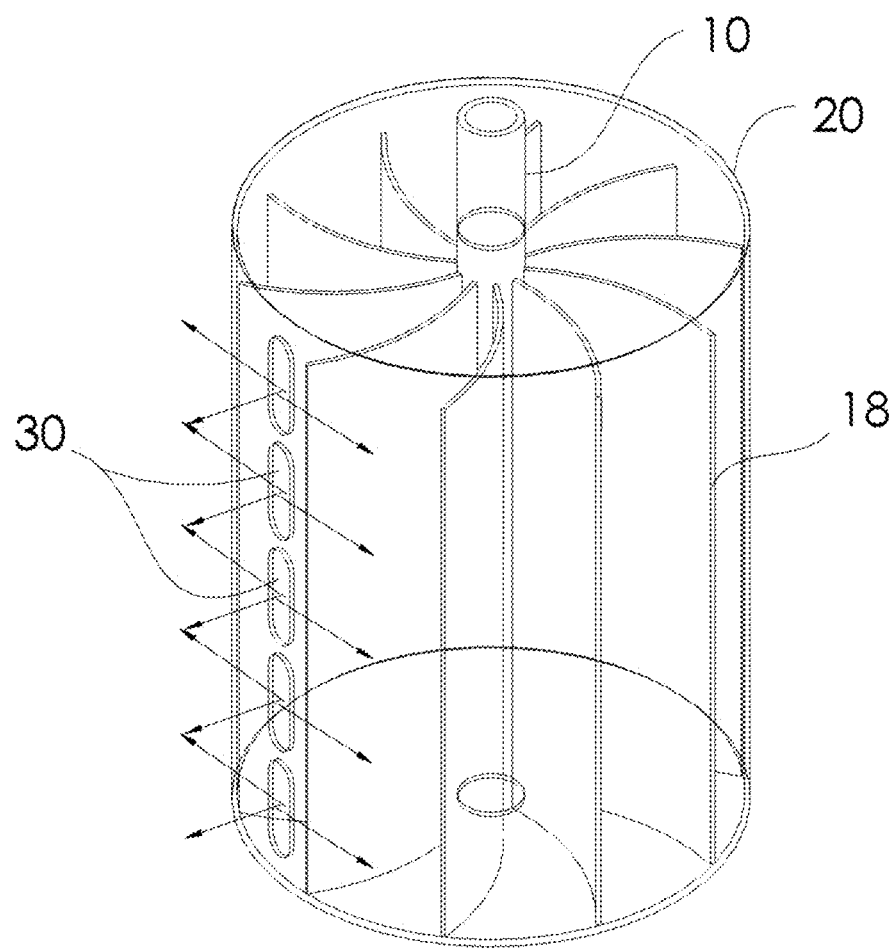
FIG. 16b is a perspective view of the centrifugation device with curved centrifugal plates, a centrifugation tank with 1-micron stainless steel filters, and without an aqueous drainage pipe according to an embodiment of the present application.

As indicated in FIGS. 16a and 16b, aqueous medium diffuses through the 1-micron stainless steel filters 30' of the centrifugation device of the present application during centrifugation. Manual drainage can be avoided and the harvest yield of biomass can be optimized.

Figure 17:
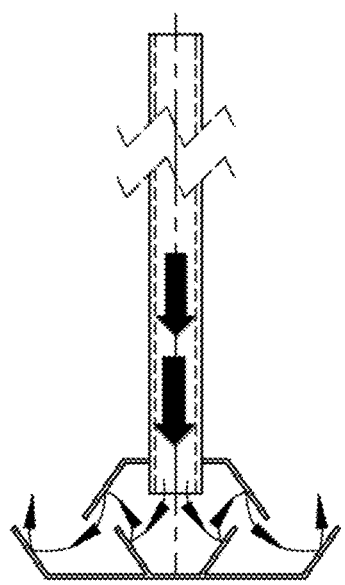
FIG. 17 is an illustrative diagram of a centrifugation device of the prior art with reflective plates at the bottom of the feeding tube.

Referring to the prior art in FIG. 17, instead of turbulators, some conventional centrifugation devices include reflective plates at the bottom of the feeding tube. Laminar flow having minor physical contact with the reflective plates may or may not be able to extract the organic matter out of the subject in the feeding medium.

Figure 18:
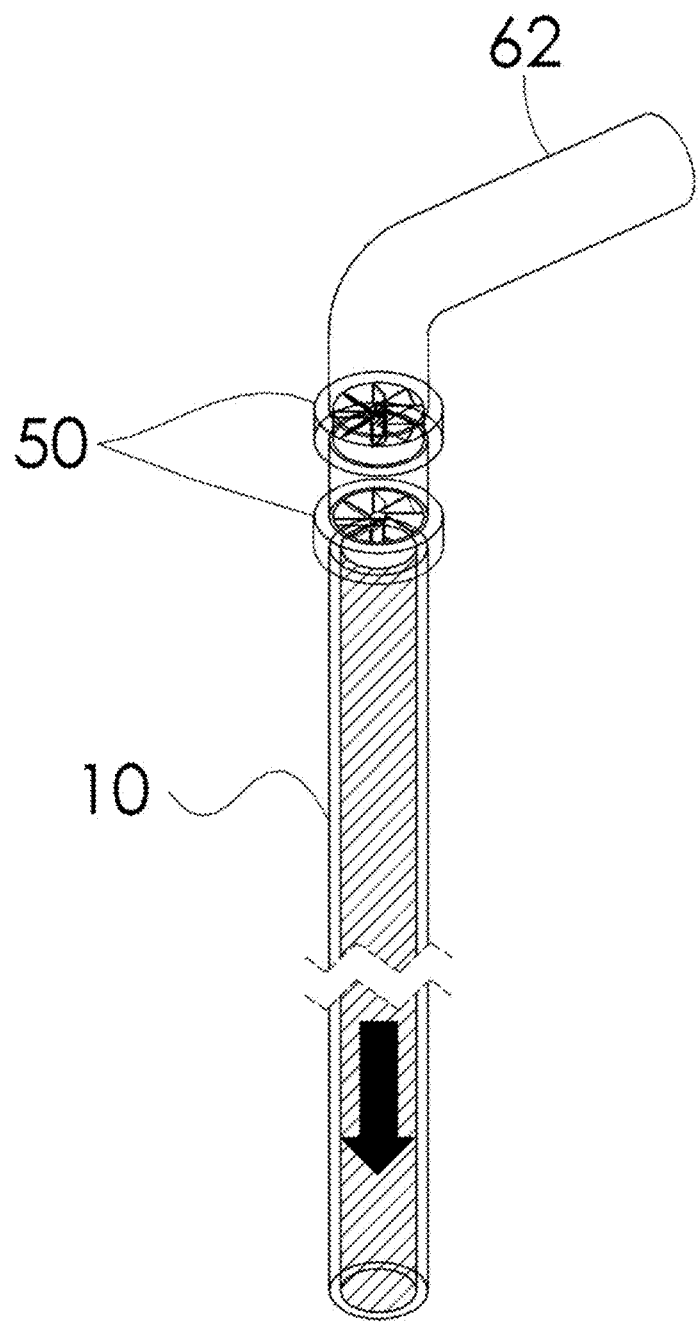
FIG. 18 is an illustrative diagram of the centrifugation device showing turbulent flow along the feeding tube according to an embodiment of the present application.

As depicted in FIG. 18, turbulent flow can be generated by the turbulators 50 of the centrifugation device of the present application to ensure the particles in the kitchen residue and/or microalgae have enough kinetic energy to collide on the adhesive and rough inner surface of the feeding tube 10, and therefore improve the efficiency of lysis of organic matter.

While the centrifugation device has been shown and described with particular references to a number of preferred embodiments thereof, it should be noted that various other changes or modifications may be made without departing from the scope of the appended claims.

What is claimed is:

1. A centrifugation device comprising:
    (a) a feeding tube defining a longitudinal axis;
    (b) a plurality of centrifugal plates extending longitudinally and radially around the feeding tube and rotatable about the longitudinal axis, the centrifugal plates having coarse surfaces coated with one or more layers of polymer material; and
    (c) a centrifugation tank disposed coaxially with the feeding tube and around the centrifugal plates, a sidewall of the tank being provided with a filter selected from the group consisting of micro filter and nano filter.

2. The centrifugation device as claimed in claim 1, wherein the polymer material comprises a mixture of polyvinyl chloride and aromatic heterocyclic polyimides.

3. The centrifugation device as claimed in claim 1, wherein the filter is a 1-micron stainless steel micro filter.

4. The centrifugation device as claimed in claim 1, wherein the filter is a polyethylene terephthalate nano filter with a pore size of 10 angstrom.

5. The centrifugation device as claimed in claim 1, further comprising one or more turbulators mounted at an inlet of the feeding tube.

6. The centrifugation device as claimed in claim 5, further comprising a reservoir for supplying a mixture to be centrifuged to the turbulators through a reservoir pipe.

7. The centrifugation device as claimed in claim 1, wherein an inner surface of the feeding tube is coated with a layer of polymer material comprising a mixture of polyvinyl chloride and aromatic heterocyclic polyimides.

8. The centrifugation device as claimed in claim 1, wherein an inner surface of the feeding tube comprises an uneven inner surface.

9. The centrifugation device as claimed in claim 1, further comprising an outer shell in which the centrifugation tank is disposed, and a container communicated with the outer shell through a pipe.

10. The centrifugation device as claimed in claim 1, wherein the thickness of the layer of polymer material is 2-3 micrometer with a micro-hardness of 1000-1200 gf.

11. The centrifugation device as claimed in claim 1, wherein the centrifugal plates are flat plates.

12. The centrifugation device as claimed in claim 1, wherein the centrifugal plates are curved plates.

13. The centrifugation device as claimed in claim 2, wherein the ratio of polyvinyl chloride and aromatic heterocyclic polyimides is 1:9.

* * * * *